(12) United States Patent
Philippe et al.

(10) Patent No.: US 6,585,962 B2
(45) Date of Patent: Jul. 1, 2003

(54) USE OF POLYAMINO ACID DERIVATIVES AS PRESERVING AGENTS, COMPOSITIONS COMPRISING THEM AND PRESERVING PROCESS USING THEM

(75) Inventors: Michel Philippe, Wissous (FR); Sylvie Benard, Attainville (FR); Sylvie Cupferman, L'Hay les Roses (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/770,472

(22) Filed: Jan. 29, 2001

(65) Prior Publication Data

US 2001/0036914 A1 Nov. 1, 2001

(30) Foreign Application Priority Data

Jan. 28, 2000 (FR) .............................................. 00 01208

(51) Int. Cl.[7] .................. A61K 31/555; A61K 6/00; A61K 7/32; A61K 7/021
(52) U.S. Cl. .................. 424/61; 424/401; 424/65; 424/63; 514/184
(58) Field of Search .................. 514/184; 424/401, 424/65, 63

(56) References Cited

FOREIGN PATENT DOCUMENTS

| EP | 0 844 057 | | 12/1998 |
|---|---|---|---|
| FR | 2 776 510 | | 10/1999 |
| JP | 4-198114 | | 7/1992 |
| JP | 6-248072 | | 9/1994 |
| JP | 7-41467 | | 2/1995 |
| WO | WO9220647 | * | 11/1992 |
| WO | WO 95/00547 | | 1/1995 |
| WO | WO9949837 | * | 10/1999 |

OTHER PUBLICATIONS

Co–pending Application No. 09/647,493; Attorney Docket No. 05725.0757–00000 International Application No. PCT/FR99/00256 Title: Polyamino Acid Derivatives and Use Thereof in Compositions for Treating Keratin Fibres Inventor(s): Michel Philippe et al. U.S. Filing Date: Dec. 14, 2000.
Co–pending Application—Attorney Docket No. 05725.0834–00000 Title: Use of Polyamino Acid Derivatives to Treat Seborrhoea and the Associated Skin Disorders Inventor(s): Michel Philippe et al. U.S. Filing Date: Jan. 29, 2001.
English language Derwent Abstract of FR 2 776 510.
English language Derwent Abstract of JP 4–198114.
English language Derwent Abstract of JP 6–248072.
English language Derwent Abstract of JP 7–41467.
English translation of WO 92/20647 (Nov. 26, 1992).

* cited by examiner

*Primary Examiner*—Jose' G. Dees
(74) *Attorney, Agent, or Firm*—Finnegan, Henderson, Farabow, Garrett & Dunner, L.L.P.

(57) ABSTRACT

Processes for preserving compositions, such as cosmetic and dermatological compositions, which may be intended for topical applications, through the use of at least one certain polyamino acid derivatives. Cosmetic and pharmaceutical compositions comprising at least one certain polyamino acid derivatives

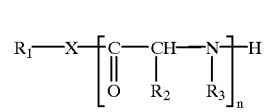

(I)

41 Claims, No Drawings

USE OF POLYAMINO ACID DERIVATIVES AS PRESERVING AGENTS, COMPOSITIONS COMPRISING THEM AND PRESERVING PROCESS USING THEM

The present invention relates to a process for preserving compositions, such as cosmetic and dermatological compositions, which may be intended for topical applications, through the use of certain polyamino acid derivatives.

It is common practice to introduce chemical preserving agents into cosmetic and dermatological compositions, these agents intended to combat the growth of microorganisms in these compositions, which would quickly make the cosmetic and dermatological compositions unsuitable for use. It is especially necessary to protect cosmetic and dermatological compositions against the microorganisms liable to grow inside the compositions and also against those which the user might introduce while handling it, such as when taking up products in jars with the fingers. Chemical preserving agents that are commonly used include parabens and formaldehyde-releasing compounds. However, these preserving agents have a drawback of causing irritation, in particular on sensitive skin, when they are present in relatively large amounts. Other known preserving agents which may be mentioned include organic hydroxy acids. However, these compounds may also cause irritation on account of their desquamating effect on the skin, which is not always well tolerated.

Thus there is a need for preserving agents, such as antimicrobial agents, whose activity is at least as effective as that of the compounds of the prior art, but which do not possess all of the drawbacks of the prior art compounds. Moreover, it would be desirable to make available antimicrobial agents whose antimicrobial spectrum is at least as broad, if not broader, than that of the compounds already known.

One aim of the present invention is thus to propose preserving agents which have a broad antimicrobial spectrum, but which do not possess all of the drawbacks of the prior art.

One subject of the present invention is the use of at least one compound chosen from polyamino acid derivatives corresponding to formula (I) as defined below, and salts thereof, as a preserving agent.

Another subject of the invention is a process for preserving a composition, such as a cosmetic or pharmaceutical composition, comprising introducing at least one polyamino acid derivative of formula (I) as defined below into the composition.

Another subject of the invention is a cosmetic and pharmaceutical composition comprising, in a physiologically acceptable medium, at least one preserving agent chosen from polyamino acid derivatives of formula (I) as defined below and salts thereof.

It has thus been found, surprisingly and unexpectedly, that certain polyamino acid derivatives may have good antimicrobial properties with respect to, for example, viruses, bacteria, yeasts and fungi/molds. On account of their broad antimicrobial spectrum, these derivatives may thus be used, for example, in cosmetic compositions as sole antimicrobial agents, such as antibacterial agents, as antiviral agents, as anti-yeast agents and as antifungal agents. Moreover, these polyamino acid derivatives may be advantageously used as preserving agents in cosmetic and pharmaceutical compositions, such as dermatological compositions.

Advantages of the polyamino acid derivatives according to the present invention, which may be based on their clearly defined and characterized chemical structure, include their manufacture being readily reproducible, and their industrial feasibility being relatively simple. Furthermore, the polyamino acid derivatives according to the present invention have good solubility and compatibility with the media commonly used in cosmetics, for example, aqueous media.

The polyamino acid derivatives used in the context of the present invention are well known in the prior art, including the cosmetics art for their moisturizing properties and for their use in haircare.

Mention may thus be made of Japanese patent application JP-07/041 467, which discloses a class of polyamino acids of high molecular weight consisting essentially of cysteine, as well as the process for preparing these polyamino acids. A class of polyamino acids characterized by the presence of thiol and disulphide functions has also been disclosed in Japanese patent application JP-06/248 072. These polyamino acids react with the thiol linkages of keratin, thus forming disulphide bridges, which makes it possible to increase the sheen and coloration qualities of the hair. Polyamino acids consisting essentially of amino acids with neutral and acidic chains have been disclosed in Japanese patent application JP-04/198 114, along with their use as moisturizing agents.

Mention may also be made of patent application FR-A-2 776 510, which discloses a cosmetic composition intended for reinforcing and caring for keratin fibres, in particular hair fibres, comprising polyamino acid derivatives.

The polyamino acid derivatives used in the context of the present invention correspond to formula (I) below:

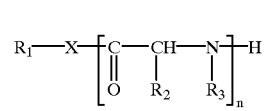

(I)

in which:

X is chosen from O, S, NH and NR", wherein R" is chosen from saturated and unsaturated, linear and branched $C_{1-6}$ hydrocarbon-based radicals;

$R_1$ is chosen from, i) linear and branched, saturated and unsaturated $C_{1-40}$ hydrocarbon-based radicals, optionally substituted with at least one hydroxyl radical and at least one radical —NRR' and optionally interrupted with at least one hetero atom chosen from N, O and Si, wherein R and R', which may be identical or different, are chosen from hydrogen and saturated and unsaturated, linear and branched $C_{1-6}$ hydrocarbon-based radicals;

ii) radicals of the formula

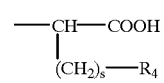

wherein s may be equal to 0, 1, 2, 3 and 4; and $R_4$ is chosen from hydrogen and radicals chosen from —$NH_2$, —OH, —SH, —$CHOHCH_3$, —$CONH_2$, —NH—$C(NH_2)$=NH, —$C_6H_5$, —$C_6H_4OH$,

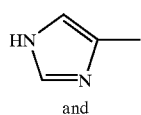

and iii) radicals of the formula

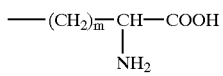

wherein m may be equal to 3, 4 and 5;
$R_2$ is chosen from hydrogen; saturated and unsaturated, linear and branched $C_{1-8}$ hydrocarbon-based radicals; radicals chosen from —$CH_2C_6H_5$, —$CH_2C_6H_4OH$, —$CH_2OH$, —$CHOHCH_3$, —$(CH_2)_t$—$NH_2$ wherein t may be equal to 3 and 5;
$R_3$ is chosen from hydrogen and saturated and unsaturated, linear and branched $C_{1-6}$ hydrocarbon-based radicals;
n is an number greater than 1 such that the number average molecular weight of the polyamino acid derivative generally ranges from 100 to 200 000;
wherein the repeating units may be identical or different for the same derivative.

For example, the repeating units may be identical. If the repeating units are different, then at least one of $R_2$ and $R_3$ may be varied between the repeating units by choosing at least one of the other meanings given for these radicals.

The salts of the polyamino acid derivatives, such as mineral acid salts and organic acid salts, also form part of the present invention.

According to one embodiment of the present invention, at least one of the following definitions apply to the polyamino acid derivatives:
X is chosen from O, S, NH and NR", wherein R" is chosen from saturated and unsaturated, linear and branched $C_{1-6}$ hydrocarbon-based radicals;
$R_1$ is chosen from linear and branched, saturated and unsaturated $C_{8-40}$ hydrocarbon-based radicals, optionally substituted with at least one hydroxyl radical and one radical NRR' and optionally interrupted with at least one hetero atom chosen from N, O and Si, wherein R and R', which may be identical or different, are chosen from hydrogen and saturated and unsaturated, linear and branched $C_{1-6}$ hydrocarbon-based radicals;
$R_2$ is hydrogen;
$R_3$ is chosen from saturated, linear and branched $C_{1-6}$ hydrocarbon-based radicals; such as, for example, methyl and ethyl radicals; and
n is chosen from a number ranging from 2 to 100, or is chosen from a number such that the number average molecular weight of the polyamino acid derivative generally ranges from 150 to 10,000. In certain embodiments, each of these definitions apply.

In another embodiment of the present invention, at least one of the following definitions apply to the polyamino acid derivatives:
X is chosen from O, S and NH;
$R_1$ is chosen from linear and branched, saturated $C_{10-24}$ hydrocarbon-based radicals, optionally substituted with 1, 2, 3 and 4 hydroxyl radicals; and linear and branched unsaturated $C_{12-24}$ hydrocarbon-based radicals, optionally substituted with at least one hydroxyl radical;
$R_2$ is hydrogen;
$R_3$ is a methyl radical; and
n is chosen from a number ranging from 4 to 50, or is chosen from a number such that the number average molecular weight of the polyamino acid derivative generally ranges from 300 to 8 000. In certain embodiments, each of these definitions apply.

The polyamino acid derivatives according to the invention may readily be prepared by those skilled in the art on the basis of their general knowledge. Patent application FR-A-2 776 510, for example, discloses a process for preparing these compounds.

The polyamino acid derivatives may be present in the compositions, such as a cosmetic and pharmaceutical composition, in an amount which is sufficient to obtain the desired effect, such as in an amount generally ranging from 0.001% to 30% by weight, for example, such as from 0.01% and 15% by weight, relative to the total weight of the composition. In one embodiment, the polyamino acid derivatives is present in the composition in an amount ranging from 0.5% to 5% by weight, relative to the total weight of the composition.

The composition comprising the polyamino acid derivatives further comprises mediums which may be cosmetically and pharmaceutically acceptable, such as. mediums which are compatible with the skin, mucous membranes, the hair and the scalp. They may be in any presentation form which is suitable for topical application. Suitable forms include aqueous, aqueous-alcoholic, organic and oily solutions; suspensions and dispersions in solvents and fatty substances; lotions and serums; vesicular dispersions; W/O, O/W, and multiple emulsions such as cream and milk; ointments, gels, solid tubes, pasty and solid anhydrous products; mousses, such as an aerosol mousse; and sprays.

The physiologically acceptable medium in which the polyamino acid derivatives may be used, and also its constituents, the amount thereof, the presentation form of the composition and the method for preparing it, may be chosen by those skilled in the art on the basis of their general knowledge depending on the desired type of composition.

For example, the composition can comprise any fatty substance usually used in the field of application envisaged. Mention may be made, for example, of silicone fatty substances such as silicone oils, gums and waxes, as well as non-silicone fatty substances such as oils and waxes of plant, mineral, animal and synthetic origin. The oils may be chosen from volatile and non-volatile oils. Mention may also be made of synthetic hydrocarbons, esters and ethers, fatty alcohols and fatty acids.

The composition can also comprise an aqueous medium, an aqueous-alcoholic medium containing an alcohol such as ethanol and isopropanol, an organic medium comprising common organic solvents such as $C_1$–$C_6$ alcohols, including ethanol and isopropanol, glycols such as propylene glycol, and ketones.

The composition can further comprise at least one conventional emulsifier chosen from amphoteric, anionic, cationic and nonionic emulsifiers, which may be used alone and as a mixture.

The composition can also comprise at least one adjuvant that is common in the field under consideration, such as hydrophilic and lypophilic thickeners and gelling agents, hydrophilic and lypophilic additives, active agents, such as cosmetic active agents, preserving agents, antioxidants, fragrances, fillers, pigments, UV screening agents, odor absorbers, dyes, moisturizers such as glycerol, vitamins, essential fatty acids, lyposoluble polymers, such as hydrocarbon-based polymers, opacifiers, stabilizers, sequestering agents, conditioners and propellants.

Needless to say, a person skilled in the art will take care to select the at least one adjuvant and the amount thereof such that the advantageous properties of the composition according to the invention are not substantially adversely affected by the addition envisaged.

The pH of the compositions according to the invention is generally less than 7. In one embodiment, the pH ranges from 3 to 6.

The polyamino acid derivatives used in the context of the present invention may have antimicrobial activity. In one embodiment, the antimicrobial activity is chosen from antibacterial activity, antiviral activity, antiyeast activity and antifungal activity.

Depending on the nature of the substituents X, $R_1$, $R_2$ and $R_3$, and on the value of "n", it has been found that it is possible to obtain compounds that are more active, and also those which are less active, with respect to a given type of microbe. The field of action of the derivatives according to the invention may thus be modified by focusing on a given microbe, and then by appropriately selecting the chemical nature of the compound used.

The polyamino acid derivatives according to the invention thus find application, for example, in compositions which may be:

in the form of make-up products for the skin of the face, of the body and of the lips, such as, for example, foundation, face powder, eye shadow, concealer sticks, cover sticks, eyeliner, mascara, lipstick, a nail varnish and a nailcare product;

in the form of dermatological and cosmetic care products for the skin of the face, of the body, including the scalp, and of the lips, such as a lipcare base, a fixing base to be applied over a conventional lipstick, antisun compositions and artificial tanning compositions; deodorant products; care compositions (day, night, anti-wrinkle, moisturizing, etc. product) for the face; matt-effect compositions for the face; cleansing and make-up-removing gel and cream; a protective body milk, a bodycare milk, and a purifying milk;

in the form of deodorant compositions; aftershave gels and lotions; and hair-removing cream;

in the form of pharmaceutical compositions;

in the form of solid composition such as cleansing soaps and bars;

in the form of aerosol compositions also comprising propellant under pressure;

in the form of haircare compositions, such as, for example, shampoo, hairsetting lotions, medicated lotions, styling creams and gel, dye compositions, such as, for example, an oxidation dye composition, optionally in the form of coloring shampoos, restructuring lotions for the hair, permanent-waving compositions, lotions and gels for preventing hair loss, antiparasitic shampoo; antidandruff lotions and shampoos; and medicated shampoo, such as an anti-seborrhoeic shampoo; and in the form of compositions for buccodental use, such as, for example, a toothpaste.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The present invention is illustrated in greater detail in the nonlimiting examples which follow.

EXAMPLE 1

The compound of formula (I) was prepared with $R_1$=$C_{15}H_{31}$CH(OH)—CH($CH_2$OH)—, X=—NH—, $R_2$=H, $R_3$=—$CH_3$ and n=14.2.

46 g (0.4 mol) of sarcosine N-carboxyanhydride were suspended in 250 ml of toluene in a 1-liter reactor under a nitrogen atmosphere. A suspension of 8.2 g (0.027 mol) of (D/L, erythro-threo) 2-aminooctadecane-1,3-diol in 250 ml of toluene was added portionwise. At the end of the addition, the reaction mixture was maintained at 80° C. for about 3 hours. The mixture was then cooled to room temperature and 200 ml of ethanol (98° C.) were added to dissolve the medium.

After evaporation of the solvents under reduced pressure and drying under vacuum, 34.5 g of a brown-coloured powder were obtained.

The index "n" was determined by NMR.

According to the same procedure as above, varying the proportion of (D/L)-2-aminooctadecane-1,3-diol, polyamino acid derivatives having the same structure but having the indices "n" below were obtained:

Example 1(a) n=9.8
Example 1(b) n=7.6

EXAMPLE 2

The compound of formula (I) was prepared with $R_1$=$C_{10}H_{21}$—CH($C_8H_{17}$)—$CH_2$—, $R_2$=H, X=—NH—, $R_3$=$CH_3$ and n=14.

46 g (0.4 mol) of sarcosine N-carboxyanhydride were suspended in 500 ml of toluene in a 1-liter reactor. 8.1 g (0.027 mol) of 2-octyldodecylamine were then added dropwise. At the end of the addition, the mixture was maintained at 80° C. for about 2 hours. It was then cooled to room temperature, followed by addition of 50 ml of ethanol (95° C.).

After evaporation of the solvents under reduced pressure and drying under vacuum, 36.7 g of a brown-coloured powder were obtained.

The index "n" was determined by NMR.

According to the same procedure as above, but varying the proportion of 2-octyldodecylamine, polyamino acid derivatives having the same structure but having the indices "n" below were obtained:

Example 2(a) n=9.6
Example 2(b) n=7.4

EXAMPLE 3

The compound of formula (I) was prepared with $R_1$=$C_{16}H_{33}$—, X=—NH—, $R_2$=H, $R_3$=—$CH_3$ and n=7.2.

This polyamino acid was obtained according to the same procedure as that described in Example 2, but by reacting 12 g (0.05 mol) of hexadecylamine with sarcosine N-carboxyanhydride.

After evaporation of the solvents and drying under vacuum, 40 g of a powder were obtained.

The index "n" was determined by NMR.

By varying the proportion of hexadecylamine, polyamino acid derivatives having the same structure but having the indices "n" below were obtained:

Example 3(a) n=9.2

Example 3(b) n=12.5

EXAMPLE 4

The compound of formula (I) was prepared with $R_1=C_8H_{17}—CH=CH—C_8H_{16}—$, $X=—NH—$, $R_2=H$, $R_3=—CH_3$ and n=7.2.

This compound was obtained according to the same procedure as that described in Example 2, but by reacting 13 g (0.05 mol) of oleylamine with sarcosine N-carboxyanhydride.

After evaporation of the solvents and drying under vacuum, 42 g of a powder were obtained.

The index "n" was determined by NMR.

By varying the proportion of oleylamine, polyamino acid derivatives having the same structure but having the indices "n" below were obtained:

Example 4(a) n=10.5

Example 4(b) n=13.2

EXAMPLE 5

The antimicrobial activity of the compound prepared in Example 4 was determined, at different concentrations of active material (A.M.).

This activity was studied with respect to 2 gram-negative bacteria (*E. coli* and *P. aeruginosa*), one gram-positive bacterium (*E. faecalis*), one yeast (*C. albicans*) and one mould (*A. niger*).

The steps for carrying out this test were as follows:

1) Culturing the microorganism: The bacteria were cultured on slanted soybean tryptocasein agar; the yeast was cultured on slanted Sabouraud agar and the mould was cultured on malt agar.

2) Preparing the inoculum: For the bacteria and the yeast: 24 hours before the start of the test, the strain was subcultured and was incubated for 24 hours at 35° C.; for the mould: 5 days. After the incubation period, the slant was washed with 9 ml of suitable diluent. The suspension obtained had a titre of $10^8$ microorganisms/ml.

3) Preparing the sample: 20 g of the composition comprising the test compound and 0.2 ml of inoculum (i.e. $10^6$ microorganisms/ml) were placed in a glass flask known as a pill bottle, homogenization was carried out and the material was incubated at 22° C., in the dark, for 7 days. In parallel, a control (placebo) was prepared to check that the microorganisms were under favourable growth conditions throughout the test.

4) Sampling and counting: After 7 days in contact, the contents of the pill bottle were homogenized and 1 g was taken therefrom. After determining the appropriate dilution to be able to carry out counting, this dilution was spread on the surface of agar Petri dishes (Eugon LT100 medium) and the Petri dishes were then incubated for 24 hours to 5 days, depending on the microorganisms, in an incubator at 35° C. The colonies on the dishes containing more than 20 and less than 200 colonies were then counted.

The test composition consisted of an aqueous solution (pH 7) of the compound of Example 4(a).

The results obtained were indicated in the table below. They were expressed as the number of microorganisms per gram of preparation:

| Test compound | E. coli | P. aeruginosa | E. faecalis | C. albicans | A. niger |
|---|---|---|---|---|---|
| Compound at 0.5% A.M. | <200 | <200 | <200 | <200 | <200 |
| Compound at 0.05% A.M. | <200 | <200 | <200 | <200 | 26,000 |
| Control | $3.1 \times 10^6$ | $2.2 \times 10^6$ | $3.1 \times 10^6$ | $2.4 \times 10^6$ | $8.0 \times 10^5$ |

It was thus found that the test compound has a very broad antimicrobial spectrum.

EXAMPLE 6

Facial Gel

| | |
|---|---|
| Polyglyceryl acrylate (Norgel) | 30% |
| Polyacrylamide/C13–Cl4 isoparaffin/Laureth-7 (Sepigel 305) | 2% |
| Silicone oil | 10% |
| Compound of Example 1a | 5% |
| Water qs | 100% |

EXAMPLE 7

Lotion

| | |
|---|---|
| Compound of Example 2a | 0.2% |
| Glycerol | 2% |
| Ethyl alcohol | 20% |
| Oxyethylenated (26 EO) oxypropylenated (26 PO) butanol, oxyethylenated (40 EO) hydrogenated castor oil in water | 1% |
| Demineralized water qs | 100% |

EXAMPLE 8

Foaming Cleansing Cream

| | |
|---|---|
| Ethylene glycol monostearate | 2% |
| Compound of Example 3a | 0.5% |
| Hydrated magnesium aluminium silicate | 1.7% |
| Hydroxypropylmethyl cellulose | 0.8% |
| Mixture of sodium cocoyl isethionate and of coconut fatty acids (Elfan AT 84 G from Akzo) | 15% |
| Stearic acid | 1.25% |
| Sodium lauryl sarcosinate at 30% in water | 10% |
| Fragrance | qs |
| Demineralized water qs | 100% |

EXAMPLE 9

Care Cream

| | |
|---|---|
| Sorbitan tristearate | 1% |
| Compound of Example 4a | 1.5% |
| Crosslinked carboxyvinyl homopolymer | 0.4% |
| Xanthan gum | 0.5% |
| Ethylene glycol dimethacrylate/lauryl methacrylate copolymer | 1% |
| Cyclopentadimethylsiloxane | 6% |
| Glycerol | 3% |
| Emulsifier | 4% |
| Fragrance | qs |
| Demineralized water    qs | 100% |

EXAMPLE 10

Medicated Gel

| | |
|---|---|
| Compound of Example 1b | 1% |
| Xanthan gum | 1% |
| Glycerol | 2% |
| Ethanol | 20% |
| Oxyethylenated (26 EO) oxypropylenated (26 PO) butyl alcohol, oxyethylenated (40 EO) hydrogenated castor oil mixture in water | 1% |
| Fragrance | qs |
| Demineralized water    qs | 100% |

EXAMPLE 11

Tinted Cream

| | |
|---|---|
| Hydrogenated lecithin | 2.4% |
| Apricot kernel oil | 6% |
| Ethylene glycol dimethacrylate/lauryl methacrylate copolymer | 1% |
| Oxyethylenated (5 EO) soybean sterols | 1.6% |
| Compound of Example 2b | 1% |
| Iron oxides | 0.9% |
| Titanium oxide | 5% |
| Polyacrylamide/$C_{13}$–$C_{14}$-isoparaffin/Laureth-7 (Sepigel 305) | 4% |
| Cyclopentadimethylsiloxane | 6% |
| Glycerol | 6% |
| Propylene glycol | 6% |
| Fragrance | qs |
| Demineralized water    qs | 100% |

EXAMPLE 12

Cover Stick

| | |
|---|---|
| Waxes (carnauba wax and ozokerite) | 14% |
| Liquid fraction of karite butter | 4% |
| Titanium oxide and zinc oxide | 22% |
| Iron oxides | 4% |
| Compound of Example 3b | 1% |
| Polydimethylsiloxane/hydrated silica | 0.1% |
| Cetyl alcohol | 1.4% |
| Isoparaffin    qs | 100% |

What is claimed is:

1. A process for preserving a composition comprising:
introducing into said composition at least one preserving agent chosen from polyamino acid derivatives of formula (I) and salts thereof,

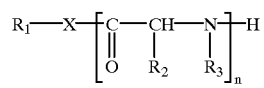
(I)

in which:
X is chosen from O, S, NH and NR″, wherein R″ is chosen from saturated and unsaturated, linear and branched $C_{1-6}$ hydrocarbon-based radicals;
$R_1$ is chosen from:
 (i) linear and branched, saturated and unsaturated $C_{1-40}$ hydrocarbon-based radicals;
 (ii) radicals of the formula

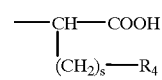

wherein s is a number chosen from 0, 1, 2, 3 and 4; and $R_4$ is chosen from hydrogen and radicals chosen from —$NH_2$, —OH, —SH, —CHOHCH$_3$, —CONH$_2$, —NH—C(NH$_2$)=NH, —$C_6H_5$, —$C_6H_4$OH and

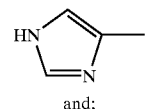

and;

(iii) radicals of the formula

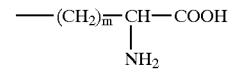

wherein m is a number chosen from 3, 4 and 5;
$R_2$ is chosen from hydrogen; saturated and unsaturated, linear and branched $C_{1-8}$ hydrocarbon-based radicals; and radicals chosen from —CH$_2$C$_6$H$_5$, —CH$_2$C$_6$H$_4$OH, —CH$_2$OH, —CHOHCH$_3$, —(CH$_2$)$_t$—NH$_2$, wherein t is a number chosen from 3 and 5;
$R_3$ is chosen from hydrogen and saturated and unsaturated, linear and branched $C_{1-6}$ hydrocarbon-based radicals; and
n is a number greater than 1 chosen such that the number average molecular weight of the polyamino acid derivative ranges from 100 to 200 000;
wherein the repeating unit may be identical or different for the same derivative.

2. A process according to claim 1, wherein said at least one preserving agent is chosen from an antimicrobial agent.

3. A process according to claim 2, wherein said antimicrobial agent is chosen from an antibacterial agent, an antiviral agent, an anti-yeast agent and an antifungal agent.

4. A process according to claim 1, wherein $R_1$ is chosen from linear and branched, saturated and unsaturated $C_{1-40}$ hydrocarbon-based radicals substituted with at least one hydroxyl radical, at least one radical —NRR′, or at least one hydroxyl radical and at least one radical —NRR′, wherein R and R′, which may be identical or different, are chosen from hydrogen and saturated and unsaturated, linear and branched $C_{1-6}$ hydrocarbon-based radicals.

5. A process according to claim 1, wherein $R_1$ is chosen from linear and branched, saturated and unsaturated $C_{1-40}$ hydrocarbon-based radicals interrupted with at least one hetero atom chosen from N, O and Si.

6. A process according to claim 1, wherein in said polyamino acid derivatives of formula (I) and salts thereof, at least one of the following definitions apply:

$R_1$ is chosen from linear and branched, saturated and unsaturated $C_{8-40}$ hydrocarbon-based radicals;

$R_2$ is hydrogen;

$R_3$ is chosen from saturated, linear and branched $C_{1-6}$ hydrocarbon-based radicals; and n is chosen from a number ranging from 2 to 100 and a number chosen such that the number average molecular weight of said polyamino acid derivative ranges from 150 to 10,000.

7. A process according to claim 6, wherein $R_3$ is chosen from methyl and ethyl radicals.

8. A process according to claim 6, wherein $R_1$ is chosen from linear and branched, saturated and unsaturated $C_{8-40}$ hydrocarbon-based radicals substituted with at least one hydroxyl radical, at least one radical —NRR', or at least one hydroxyl radical and at least one radical —NRR', wherein R and R', which may be identical or different, are chosen from hydrogen and saturated and unsaturated, linear and branched $C_{1-6}$ hydrocarbon-based radicals.

9. A process according to claim 6, wherein $R_1$ is chosen from linear and branched, saturated and unsaturated $C_{8-40}$ hydrocarbon-based radicals interrupted with at least one hetero atom chosen from N, O and Si.

10. A process according to claim 6, wherein $R_1$ is chosen from linear and branched, saturated and unsaturated $C_{8-40}$ hydrocarbon-based radicals;

$R_2$ is hydrogen;

$R_3$ is chosen from saturated, linear and branched $C_{1-6}$ hydrocarbon-based radicals; and n is chosen from a number ranging from 2 to 100 and a number chosen such that the number average molecular weight of said polyamino acid derivative ranges from 150 to 10,000.

11. A process according to claim 1, wherein in said polyamino acid derivatives of formula (I) and salts thereof, at least one of the following definitions apply:

X is chosen from O, S and NH;

$R_1$ is chosen from linear and branched, saturated $C_{10-24}$ hydrocarbon-based radicals; and linear and branched unsaturated hydrocarbon-based radicals;

$R_2$ is hydrogen;

$R_3$ is a methyl radical; and n is chosen from a number ranging from 4 to 50 and a number chosen such that the number average molecular weight of said polyamino acid derivative ranges from 300 to 8,000.

12. A process according to claim 11, wherein X is NH.

13. A process according to claim 11, wherein $R_1$ is chosen from linear and branched, saturated $C_{10-24}$ hydrocarbon-based radicals substituted with at least one hydroxyl radical.

14. A process according to claim 13, wherein said linear and branched, saturated $C_{10-24}$ hydrocarbon-based radicals are substituted with 1, 2, 3, or 4 hydroxyl radicals.

15. A process according to claim 11, wherein $R_1$ is chosen from linear and branched unsaturated hydrocarbon-based radicals substituted with at least one hydroxyl radical.

16. A process according to claim 1 further comprising a physiologically acceptable medium.

17. A process according to claim 1, wherein said preserving agent is present in said composition in an amount ranging from 0.001% to 30% by weight, relative to the total weight of the composition.

18. A process according to claim 17, wherein said preserving agent is present in said composition in an amount ranging from 0.01% to 15% by weight, relative to the total weight of the composition.

19. A process according to claim 18, wherein said preserving agent is present in said composition in an amount ranging from 0.5% to 5% by weight, relative to the total weight of the composition.

20. A process according to claim 1, wherein said composition is chosen from a cosmetic composition and a pharmaceutical composition.

21. A process according to claim 6, wherein said composition is chosen from a cosmetic composition and a pharmaceutical composition.

22. A process according to claim 11, wherein said composition is chosen from a cosmetic composition and a pharmaceutical composition.

23. A process according to claim 1, wherein said composition is in the form of a make-up product applied to at least one area of the body chosen from the skin of the face, the skin of the body, and the lips.

24. A process according to claim 23, wherein said makeup product is chosen from a foundation, a face powder, an eye shadow, a concealer stick, a cover stick, an eyeliner, a mascara, a lipstick, a nail varnish and a nailcare product.

25. A process according to claim 1, wherein said composition is in the form of a dermatological or cosmetic care product for the skin of the face, the skin of the body, or the lips.

26. A process according to claim 25, wherein said composition is in the form of a dermatological or cosmetic care product for the skin of the scalp.

27. A process according to claim 25, wherein said dermatological or cosmetic care product is chosen from a lipcare base, a fixing base to be applied over a conventional lipstick, an antisun composition, an artificial tanning composition, a deodorant product, a care composition for the face, a matte-effect composition for the face, a cleansing gel, a cleansing cream, a make-up-removing gel, a make-up-removing cream, a protective body milk, a bodycare milk, and a purifying milk.

28. A process according to claim 27, wherein said care composition for the face is chosen from a day product and a night product.

29. A process according to claim 27, wherein said care composition for the face is an anti-wrinkle product.

30. A process according to claim 1, wherein the form of said composition is chosen form a deodorant composition, an aftershave gel, an aftershave lotion, and a hair-removing cream.

31. A process according to claim 1, wherein said composition is in the form of a pharmaceutical composition.

32. A process according to claim 1, wherein said composition is in the form of a solid.

33. A process according to claim 32, wherein said solid is chosen from a cleansing soap and a cleansing bar.

34. A process according to claim 1, wherein said composition is in the form of an aerosol comprising a propellant under pressure.

35. A process according to claim 1, wherein said composition is in the form of a haircare composition.

36. A process of claim 30, wherein said haircare composition is chosen from a shampoo, a hairsetting lotion, a medicated lotion, a styling cream, a styling gel, a dye composition, a restructuring lotion for the hair, a permanent-waving composition, a lotion for preventing hair loss, a gel for preventing hair loss, an antiparasitic shampoo; an anti-dandruff lotion, an antidandruff shampoo; and a medicated shampoo.

37. A process according to claim 36, wherein said dye composition is an oxidation dye composition.

38. A process according to claim 36, wherein said dye composition is a coloring shampoo.

39. A process according to claim 36, wherein said medicated shampoo is an anti-seborrhoeic shampoo.

40. A process according to claim 1, wherein said composition is in the form of a buccodental composition.

41. A process according to claim 40, wherein said buccodental composition is a toothpaste.

\* \* \* \* \*